United States Patent [19]

Osterlind

[11] Patent Number: 5,951,515
[45] Date of Patent: Sep. 14, 1999

[54] MEDICAL NEEDLE GUARD FOR CATHETER PLACEMENT

[75] Inventor: Roland J. Osterlind, Hoeganaes, Sweden

[73] Assignee: Becton, Dickinson and Company, Franklin Lakes, N.J.

[21] Appl. No.: 08/813,746

[22] Filed: Mar. 7, 1997

[30] Foreign Application Priority Data

Mar. 12, 1996 [GB] United Kingdom .................. 9605206

[51] Int. Cl.$^6$ ........................... A61M 5/00; A61M 5/178
[52] U.S. Cl. ...................... 604/110; 604/164; 604/198; 604/263; 128/919
[58] Field of Search .................... 604/263, 110, 604/198, 192, 164, 165, 167, 171, 195, 162, 158; 128/919

[56] References Cited

U.S. PATENT DOCUMENTS

| Re. 34,223 | 4/1993 | Bonaldo ................................. 604/164 |
| 4,834,718 | 5/1989 | McDonald . |
| 4,850,961 | 7/1989 | Wanderer et al. .................... 604/164 |
| 4,944,725 | 7/1990 | McDonald . |
| 5,019,049 | 5/1991 | Haining ................................ 604/165 |
| 5,135,505 | 8/1992 | Kaufman .............................. 604/263 |
| 5,186,712 | 2/1993 | Kelso et al. .......................... 604/177 |
| 5,192,275 | 3/1993 | Burns .................................... 604/263 |
| 5,273,540 | 12/1993 | Luther et al. ........................ 604/110 |
| 5,279,591 | 1/1994 | Simon .................................. 604/192 |
| 5,295,963 | 3/1994 | Deeks ................................... 604/110 |
| 5,300,045 | 4/1994 | Plassche, Jr. ........................ 604/158 |
| 5,312,359 | 5/1994 | Wallace ............................... 604/164 |
| 5,328,482 | 7/1994 | Sircom et al. ....................... 604/263 |
| 5,447,501 | 9/1995 | Karlsson et al. .................... 604/263 |
| 5,456,668 | 10/1995 | Ogle, II .............................. 604/110 |
| 5,672,160 | 9/1997 | Österlind et al. .................... 604/263 |
| 5,697,907 | 12/1997 | Gaba ................................... 604/198 |

FOREIGN PATENT DOCUMENTS

| 2 292 525 | 2/1996 | United Kingdom . |
| 2292525 | 2/1996 | United Kingdom . |
| WO 92/22344 | 12/1992 | WIPO . |
| WO 95/23003 | 8/1995 | WIPO . |

*Primary Examiner*—Ronald Stright, Jr.
*Attorney, Agent, or Firm*—Eric M. Lee

[57] ABSTRACT

A side button is located at the distal end of a housing forming part of an I.V. catheter and which is movable between a first position to allow longitudinal movement of a needle ands a second position preventing movement of the needle. The side button is provided with a latching member which prevents release of a cannula assembly from its hub support unless the needle is fully retracted within the housing and the side button is in its second position.

4 Claims, 9 Drawing Sheets

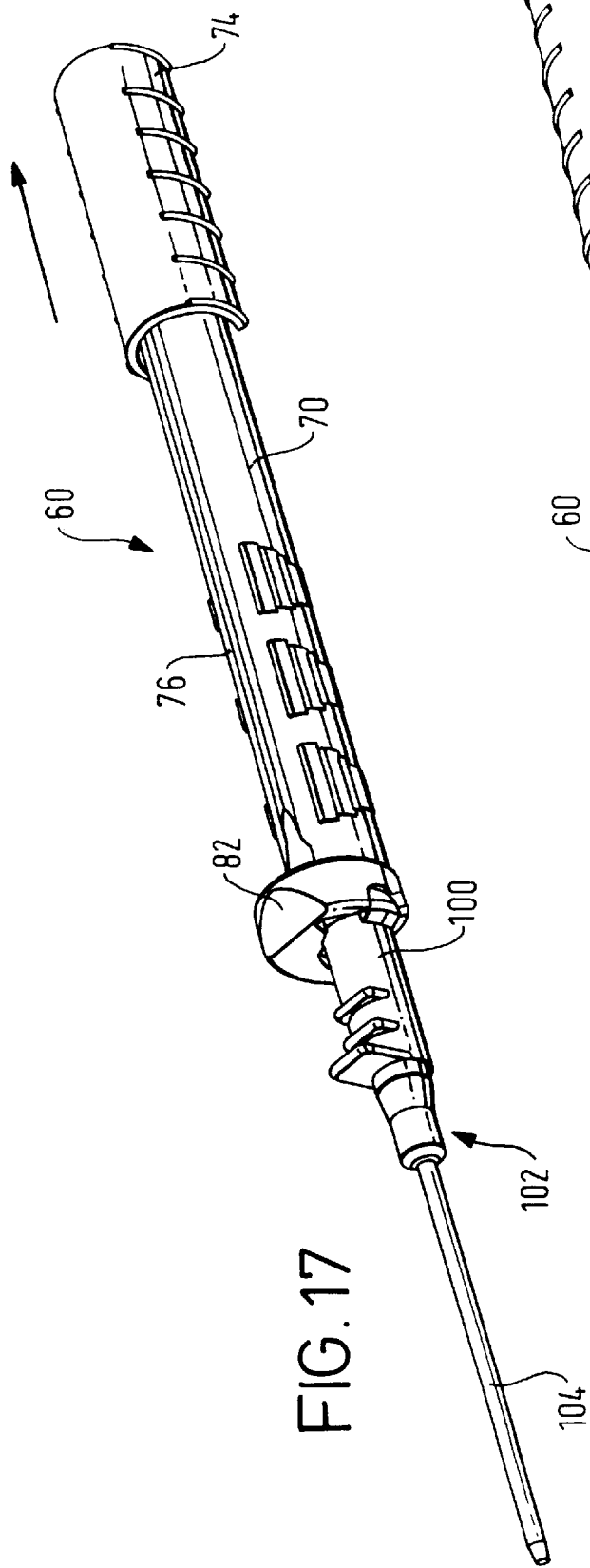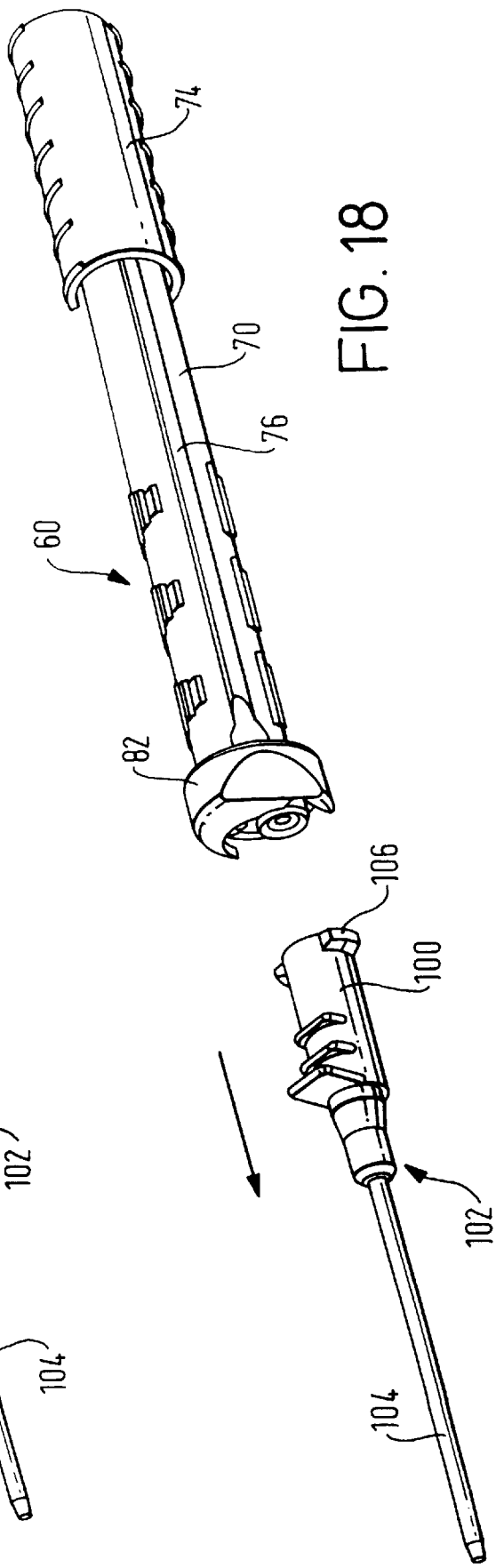

MEDICAL NEEDLE GUARD FOR CATHETER PLACEMENT

FIELD OF THE INVENTION

The present invention relates to medical devices and, in particular, to medical devices such as intravenous catheters which include a hollow needle having a sharp distal end or tip for piercing the skin of a patient.

BACKGROUND OF THE INVENTION

The existence of infectious diseases such as AIDS and hepatitis has highlighted the danger to which medical personnel may be exposed when treating patients by means of catheter devices where a sharp needle tip is used to pierce the skin of a patient. Medical personnel have been infected by physical contact with, or accidental prick by an infected needle (needle-stick).

In order to protect medical personnel against inadvertent needle-stick, a number of solutions have been developed whereby a protective means incorporated within the catheter prevents physical contact with the needle after use and hence against inadvertent needle-stick.

One known device for protecting the needle ,both before and after use, is described in European Patent Publication Number 0599564 in which a needle is arranged within a housing and is displaceable between a first retracted position and a second extended position. Means is provided for displacing the needle between said first and second positions. A sealing means for sealing the initially open distal end of the housing, is connected to the displacing means, at least initially. The sealing means during displacement of the needle from said first retracted position to said second position, is moved in the direction towards the open distal end of the housing to a sealing position and is then fixed in said sealing position, substantially sealing the interior of the housing.

The structure described in European Patent Publication Number 0599564, although effective to prevent inadvertent needle-stick, is complicated and relatively expensive to manufacture. Furthermore, the structure does not give any clear visible sign to show the user that the needle is locked in the protected position.

Another known device for protecting against inadvertent needle-stick is described in U.S. Pat. No. 5,447,501. In this document, there is described an infusion catheter assembly including a hollow needle having a sharpened distal tip for piercing the skin of a patient. The needle is mounted on a hub forming part of a casing. A needle protection device is attached to the hub and includes a rigid front end and a rear flexible end. The rigid front end incorporates a resilient member which, in a needle protected position of the needle, prevents movement of the needle in a longitudinal sense. Furthermore, the rigid front end also includes a forwardly extending boss for supporting a cannula hub forming part of a cannula assembly.

This device is a relatively simple and economic device and is effective to minimize the danger of inadvertent needle stick.

However, there is a risk that the user could attempt to disengage the cannula hub from the rigid front end before the needle is completely withdrawn inside the protection device and locked therein.

It is an aim of the present invention to provide a simple but effective means for protecting the point of a needle forming part of a medical device, such as an intravenous catheter assembly, and to provide means which prevents the user from disengaging a cannula hub from the catheter assembly before the needle is completely withdrawn inside a protective housing.

SUMMARY OF THE INVENTION

According to the present invention, a medical device comprises a hollow needle having a sharpened distal tip for piercing the skin of a patient, means for moving the needle relative to a housing between a first ready-for-use position and a second retracted needle protected position, a member mounted at the distal end of the housing and movable between a first position to allow longitudinal movement of the needle and a second position for preventing movement of the needle from its needle protected position, and a hub support member adjacent the distal end of the housing for supporting a cannula assembly characterized by means which prevents release of the cannula assembly from the hub support member until the needle is in its second retracted needle protected position.

In one embodiment, the means is a latching member forming part of the member which engages a flange forming part of the cannula assembly in the first position of the member.

Preferably, the member is mounted for sliding movement between the hub support member and the housing, the member having a through hole which, in the first position of the member, is aligned with a through hole in the hub support member to permit longitudinal movement of the needle therethrough.

Preferably, the hub support member and the member are each provided with cooperating latching means which, in the second position of the member, engage to prevent movement of the member from said second position towards said first position.

In an alternative embodiment, the means is a flange forming part of the member which engages a latching ear forming part of the cannula assembly in the first position of the member.

Preferably, the member is rigidly fixed to the housing, said member and the housing being rotatable relative to the hub support member, the hub support member having a through hole which in the first position of the member is aligned with a through hole in the member to permit longitudinal movement of the needle therethrough, rotational movement of the member from its first position to its second position causing the through holes to be misaligned thereby preventing movement of the needle from its needle protected position.

Preferably, the hub support member and the member are each provided with cooperating means which, in the second position of the member, engage to prevent movement of the member from its second position towards its first position.

BRIEF DESCRIPTION OF THE DRAWINGS

Embodiments of the invention will now be described by way of example, reference being made to the Figures of the accompanying diagrammatic drawings in which:

FIG. 17 is a perspective view of the infusion catheter assembly of FIG. 13 with its needle in a needle-protected position but with a cannula assembly still locked in position;

FIG. 18 is a perspective view similar to FIG. 17 but illustrating the cannula assembly separated from the remainder of the infusion catheter assembly and FIG. 19 is a cross-sectional detail of the catheter assembly of FIG. 13 when in the ready-for-use position.

DETAILED DESCRIPTION OF THE INVENTION

Figure 1:
FIG. 1 is a plan view of an infusion catheter assembly with its needle in a ready for penetration position.
Figure 2:
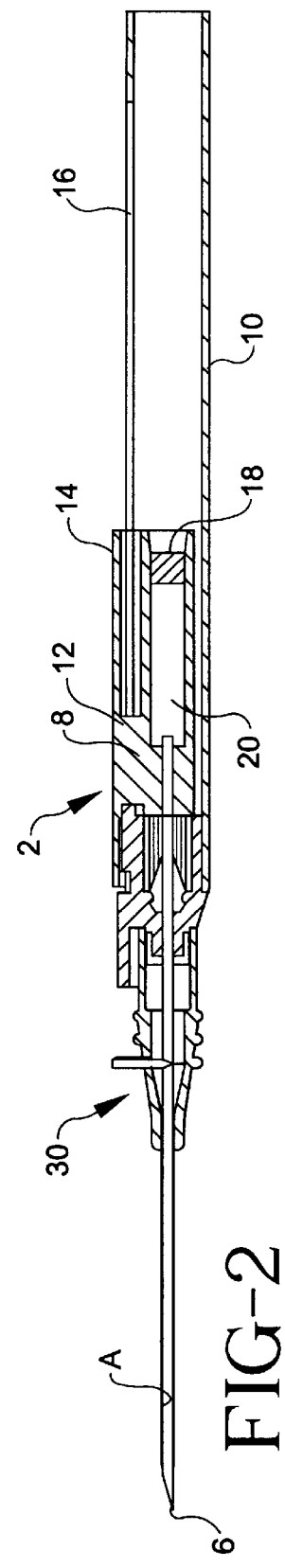
FIG. 2 is a longitudinal cross-section in elevation of the catheter assembly of FIG. 1.
Figure 3:
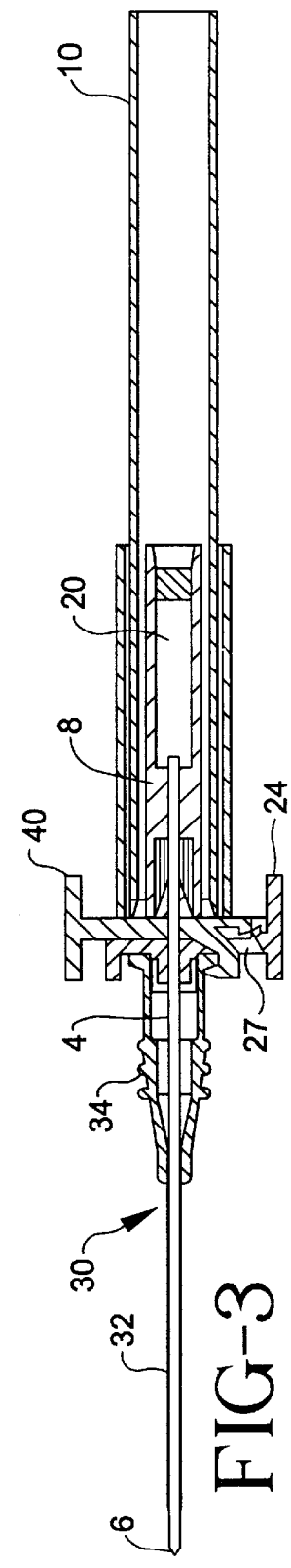
FIG. 3 is a further longitudinal cross-section on the line 33 through the catheter assembly of FIG. 1.

Referring first to the embodiment illustrated in FIGS. 1 to 8, an infusion catheter assembly 1 includes a needle assembly 2 comprising a hollow needle 4 having a sharpened distal tip 6, said needle 4 extending forwardly from a needle hub 8. The needle hub 8 is located for sliding movement within a housing 10 and includes a lug 12 supporting a serrated gripper 14. As shown most clearly in FIG. 2, the lug 12 extends through a slot 16 formed in the housing 10 in order that the gripper 14 can be engaged to reciprocate the needle hub 8 forwardly and rearwardly along the length of the housing 10. The forward facing end of the needle hub 8 is formed with a hollow protuberance 17. The needle hub 8 is hollow and is closed by a filter 18 which together with the hub 8 defines a blood flashback chamber 20.

The forward distal end of the housing 10 is effectively closed by a hub support member 24 connected thereto. However, the member 24 is formed with a through hole 26 to allow the passage therethrough of the needle 4. The forward face of the member 24 is formed with a forwardly extending boss 25 for supporting the proximal end of a cannula assembly 30. As is well known in the art, the cannula assembly 30 comprises a hollow cannula 32 attached to a cannula hub 34. The proximal end of the cannula hub 34 is provided with a flange 36. The member 24 is also formed with a through slot 27, one end of which is defined by an arm 28, having a free end formed with a protuberance 29.

Figure 4:
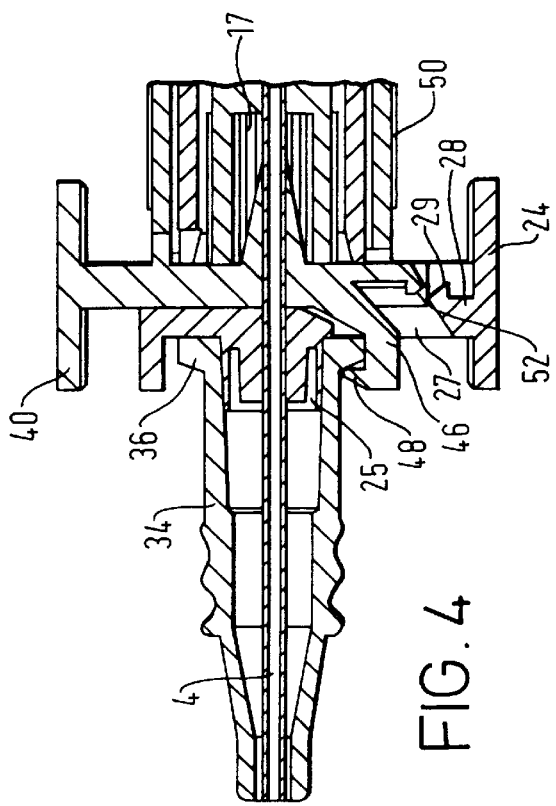
FIG. 4 is an enlarged cross-sectional detail of the catheter assembly of FIG. 3.

Mounted for sliding movement between the hub support member 24 and the remainder of the housing 10 is a button member 40. Extending rearwardly from the button member 40 is a conical boss 44 which is positioned and dimensioned to extend into the hollow protuberance 17 at the forward end of the needle hub 8 as best illustrated in FIG. 4. A through bore 42 extends completely through the boss 44 and the button member 40 and in a first position of the button member, is aligned with the hole 26 in the hub support member 24 for the passage therethrough of the needle 4 (see FIGS. 3 and 4).

Figure 6:
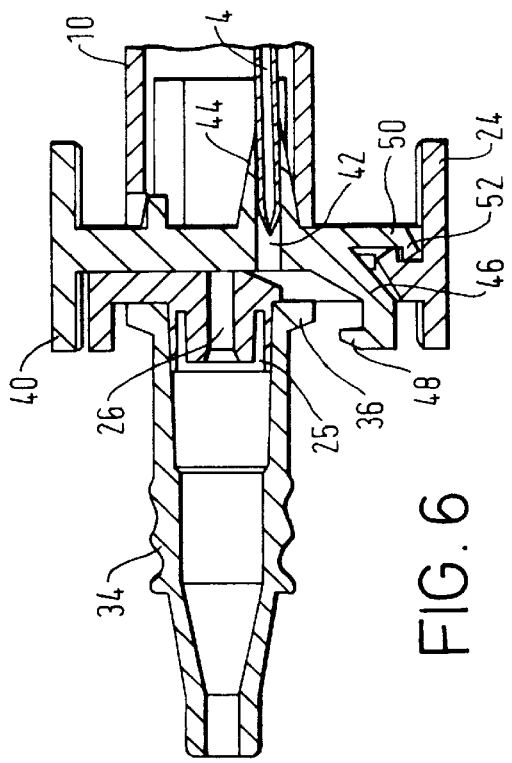
FIG. 6 is an enlarged cross-sectional detail of the catheter assembly of FIG. 6.
Figure 8:
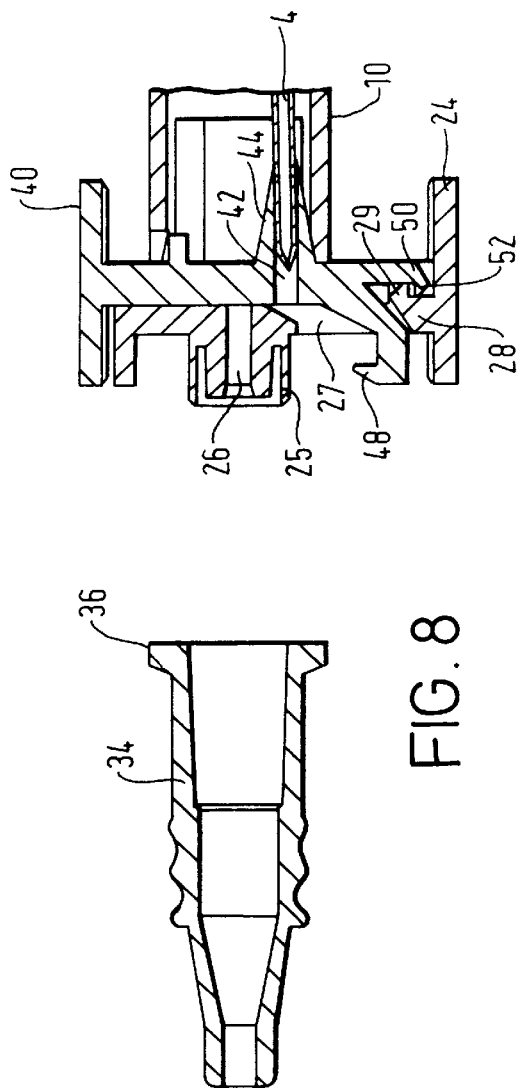
FIG. 8 is an enlarged cross-sectional detail similar to FIG. 6, but showing the cannula assembly released from the remainder of the catheter assembly.

As best shown in FIGS. 4, 6 and 8, the button member 40 includes a first arm 46 which extends through the slot 27 in the hub support member 24 and is formed at its free end with a latching member 48. Likewise, a second resilient arm 50 is provided which at its free end is formed with a latching member 52 for co-operating with the protuberance 29 of arm 28.

Referring in particular to FIGS. 1 to 4, in the ready-for-use position, the needle hub 8 is located at the forward end of the housing 10 and the button member 40 is in its first position such that the needle 4 extends through the hole 26, bore 42 and through the cannula assembly 30, so that the distal tip 6 of the needle 4 extends beyond the free distal end of the hollow cannula 32. In this position, the flank of the needle 4 will prevent movement of the button member 40 and as shown most clearly in FIG. 4, the latching member 48 will engage the flange 36 of the cannula hub 34 in order to retain the cannula hub 34 mounted on the boss 25 of the hub support member 24.

Figure 5:
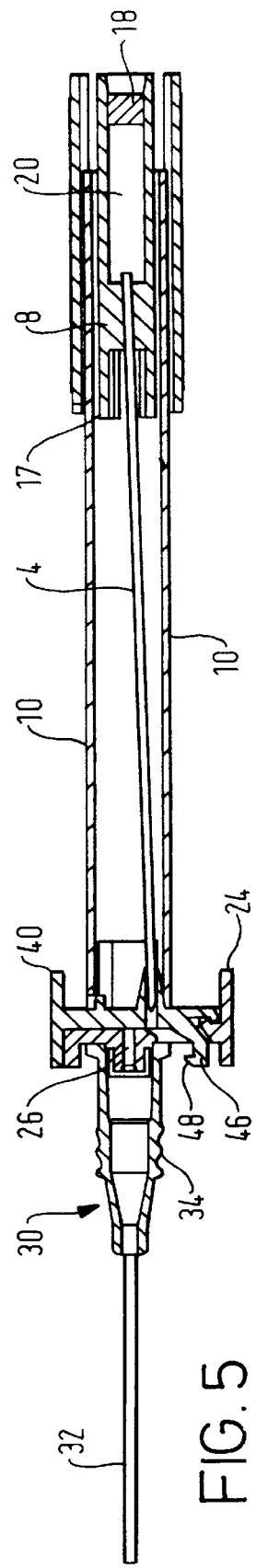
FIG. 5 is a longitudinal cross-section similar to FIG. 3, but showing the needle after use in a needle protected position and a cannula assembly remaining connected to the remainder of the catheter assembly.
Figure 7:
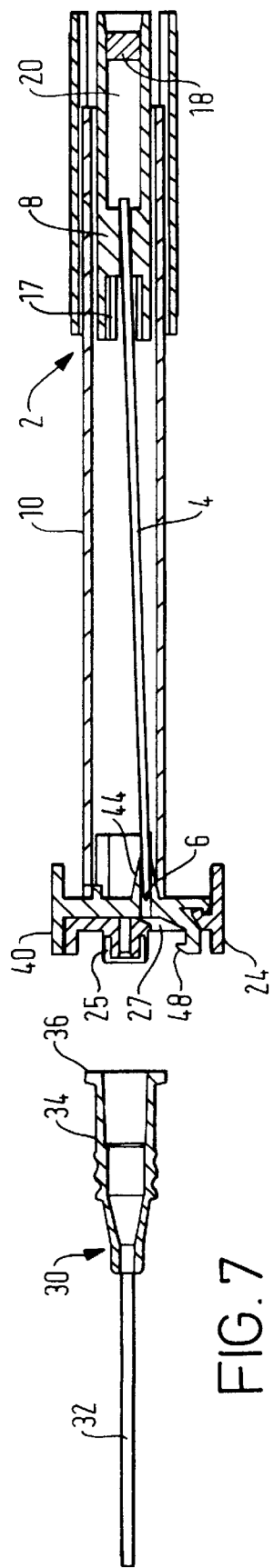
FIG. 7 is a longitudinal cross-section similar to FIGS. 5, but showing the cannula assembly released from the remainder of the catheter assembly.

Once penetration of the patient's skin has been effected, the gripper 14 is engaged to move the needle hub 8 along and towards the proximal end of the housing 10, that is, towards the position as illustrated in FIG. 5. This movement of the needle hub 8 will cause the needle 4 to be withdrawn through the hollow cannula 32, cannula hub 34, back past the hole 26 in the hub support member 24, until the sharpened distal tip 6 is located in the through bore 42 (see FIGS. 5 and 6). At this time, it should be noted that the latching means 48 still engages the flange 36 of the cannula hub 34.

Since the needle 4 is now clear of the hole 26, the button member 40 can now be moved from its first position (see FIG. 4) to a second position (see FIGS. 6 and 8) in which second position the bore 42 in which the needle tip 6 is located, will be moved laterally out of alignment with the hole 26 thereby preventing movement of the needle 4 from the housing 10. The clearance between the interior of the hollow protuberance 17 and the outer surface of the needle 4 is such that a degree of lateral movement of the needle tip 6 can be accommodated before the needle 4 will break or become detached from the needle hub 8. Movement of the button member 40 from said first to said second position, causes the latching member 48 to disengage from the flange 36 of the cannula hub 34 thereby allowing the cannula assembly 30 to be separated from the remainder of the catheter assembly 1 (see FIGS. 7 and 8). It follows, therefore, that the cannula assembly 30 can only be detached from the remainder of the catheter assembly 1 after the needle tip 6 is completely contained within the housing 10. Further, in the second position of the button member 40, the latching member 52 will engage the protuberance 29 on the arm 28 to prevent reverse movement of the button member 40 from said second to said first position thereby ensuring that the needle tip 6 cannot be inadvertently moved from its needle protected position.

In the above described embodiment, the button member 40 is moved manually from its first position (see for example FIG. 4) towards its second position (see for example FIG. 6 or FIG. 8). In a modification as illustrated in FIGS. 9 to 12, movement of the button member from its first to its second position is automatic as will now be explained.

Referring now to FIGS. 9 to 12 where like reference numerals denote like parts, an infusion catheter 1' includes a needle assembly 2 comprising a hollow needle 4 having a sharpened distal tip 6, said needle extending forwardly from a needle hub 8. The needle hub 8 is located for sliding movement within a housing 10 in a manner described with reference to the previous embodiment. The needle hub 8 is hollow and is closed by a filter 18 which together with the hub 8 defines a blood flash back chamber 20.

The forward distal end of the housing 10 is effectively closed by a hub support member 24'. The hub support member 24' has a forward face formed with a forwardly extending boss 25 for supporting the proximal end of a cannula assembly 30. The hub support member 24' also has a rearward face formed with a rearwardly (as shown) conical boss 44'. The forward and rearward faces of the hub support member 24' define between them a channel 200. Aligned through holes 26',42' are formed in the forward and rearward faces as shown most clearly in FIGS. 10 and 12.

Mounted for sliding movement along the channel 200 is a button member 40'. The button member 40' includes an arm 46' formed at its free end with a latching member 48 and a through hole 204. Located above (as shown) the button member 40' in the channel 200 is a resilient member in the form of a compression spring 202.

Figure 9:
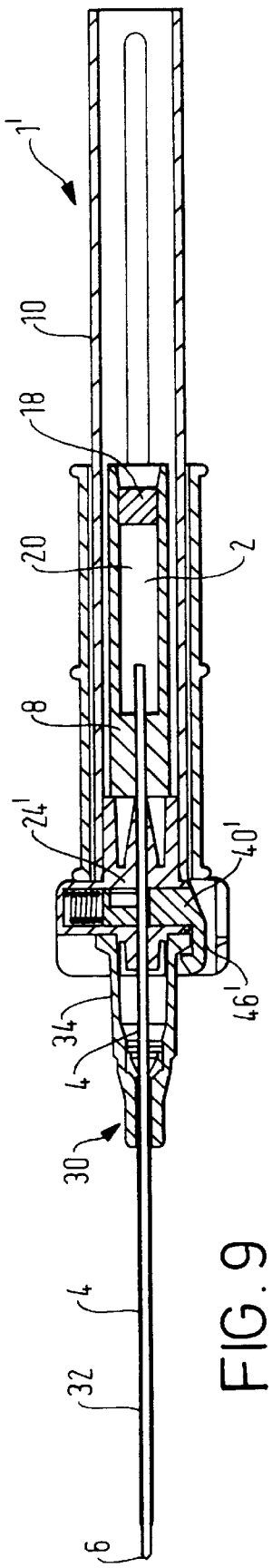
FIG. 9 is a longitudinal cross-section similar to FIG. 3, but illustrating a modified infusion catheter assembly.
Figure 10:
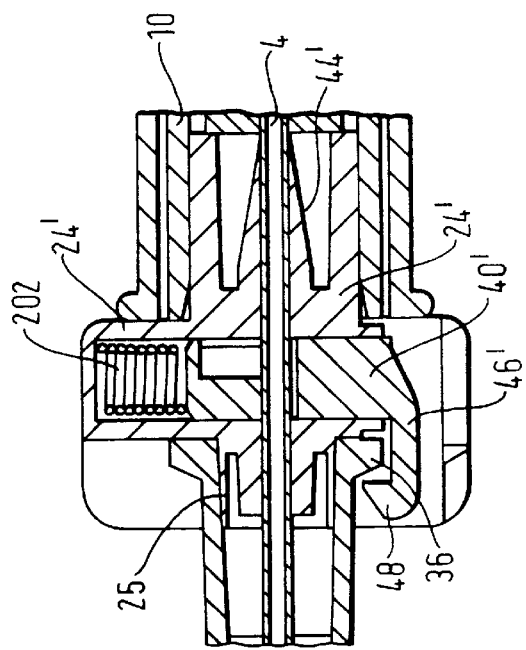
FIG. 10 is an enlarged cross-sectional detail of the catheter assembly of FIG. 9.

Referring in particular to FIGS. 9 and 10, in the ready-for-use position, the needle hub 8 is located at the forward end of the housing 10 and the button member 40' is in its first position such that the needle extends through the holes 42', 204 and 26' and then through the cannula assembly 30 so that the distal tip 6 of the needle 4 extends beyond the free distal end of the hollow cannula 32. In this position, the flank of the needle 4 will prevent movement of the button member 40' and, as shown most clearly in FIG. 10, the latching member 48 will engage a flange 36 of the cannula hub 34 in order to retain the cannula hub 34 mounted on the boss 25 of the hub support member 24'.

Figure 11:
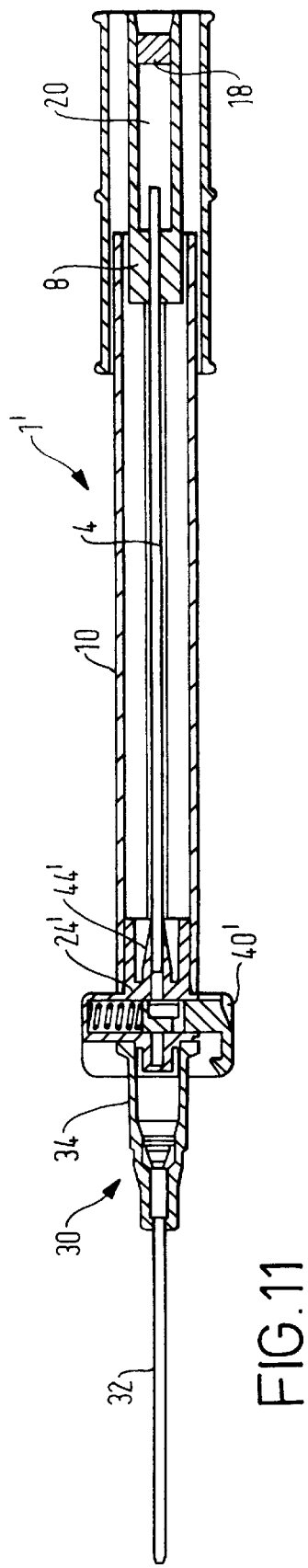
FIG. 11 is a longitudinal cross-section similar to FIG. 9, but showing the needle after use in a needle protected position.
Figure 12:
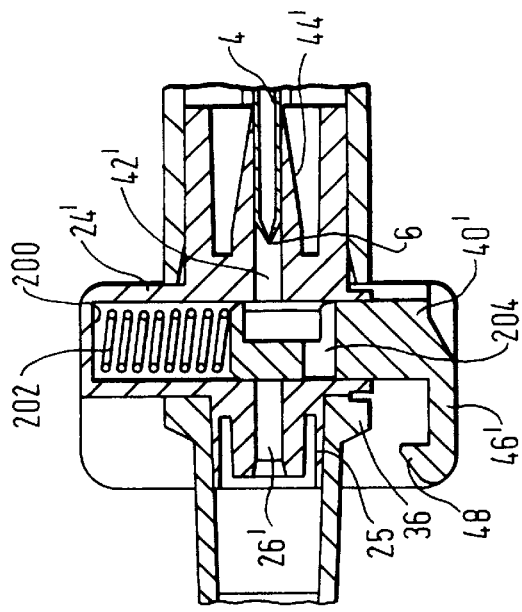
FIG. 12 is an enlarged cross-sectional detail of the catheter assembly of FIG. 11.

Once penetration of the patient's skin has been effected, the needle hub 8 is moved rearwardly along and towards the proximal end of the housing 10 (see FIG. 11). This movement of the needle hub 8 will cause the needle 4 to be withdrawn through the hollow cannula 32, cannula hub 34, back past the hole 26' in the forward face of the hub support member 24', through the hole 204 in the button member 40' until the sharpened distal tip is located in the hole 42' (see FIG. 12). Just as soon as the needle tip 6 clears the hole 204 the button member 40' will move from its first towards its second position biased by the compression spring 202.

This movement of the button member 40' from its first to its second position is automatic and, as with the first described embodiment, the latching member 48 is now disengaged from the flange 36 of the cannula hub 34 thereby allowing the cannula assembly 30 to be separated from the remainder of the catheter assembly 1'. Further, compression spring 202 will maintain the button member 40' in its second position where the hole 204 is out of alignment with the holes 26' and 42' which ensures that the needle 2 cannot be inadvertently moved from its needle protected position.

Referring now to the embodiment illustrated in FIGS. 13 to 16, an infusion catheter assembly 60 includes a needle assembly 62 comprising a hollow needle 64 having a sharpened distal tip 66. The needle 64 as shown in FIGS. 10 and 11 in a ready-for-use position extends forwardly from a needle hub 68. The needle hub 68 is located for sliding movement within a housing 70 and includes a lug 72 supporting a serrated gripper 74. As shown most clearly in FIG. 14, the lug 72 extends through a slot 76 formed in the housing 70 in order that the gripper 74 can be engaged to reciprocate the needle hub 68 forwardly and rearwardly along the length of the housing 70. The needle hub 68 is hollow and is closed by filter 78 which together with the needle hub 68 defines a blood flashback chamber 80.

Figure 13:
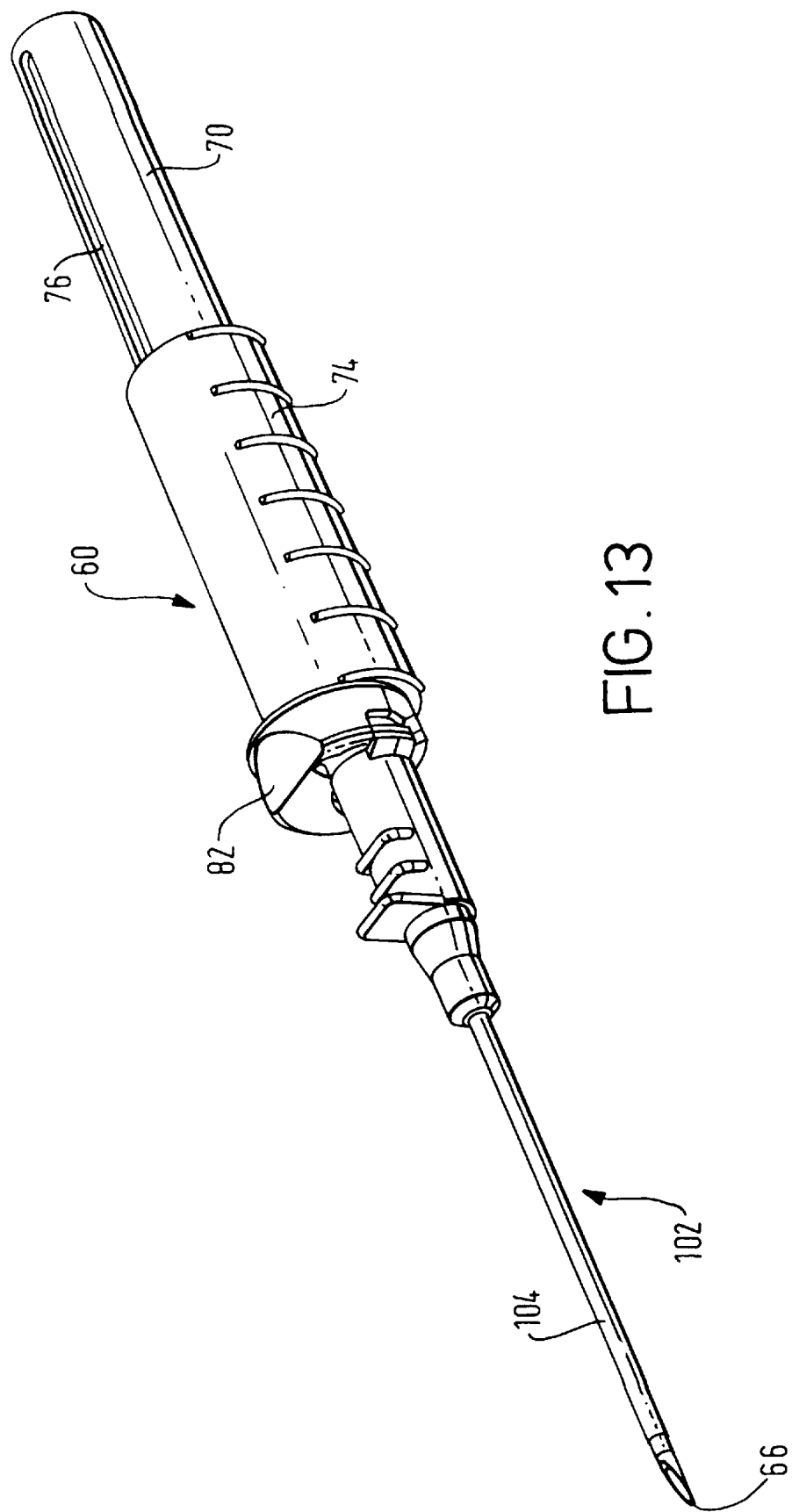
FIG. 13 is a perspective view of a second embodiment of an infusion catheter assembly with its needle in a ready-for-use position.
Figure 16:
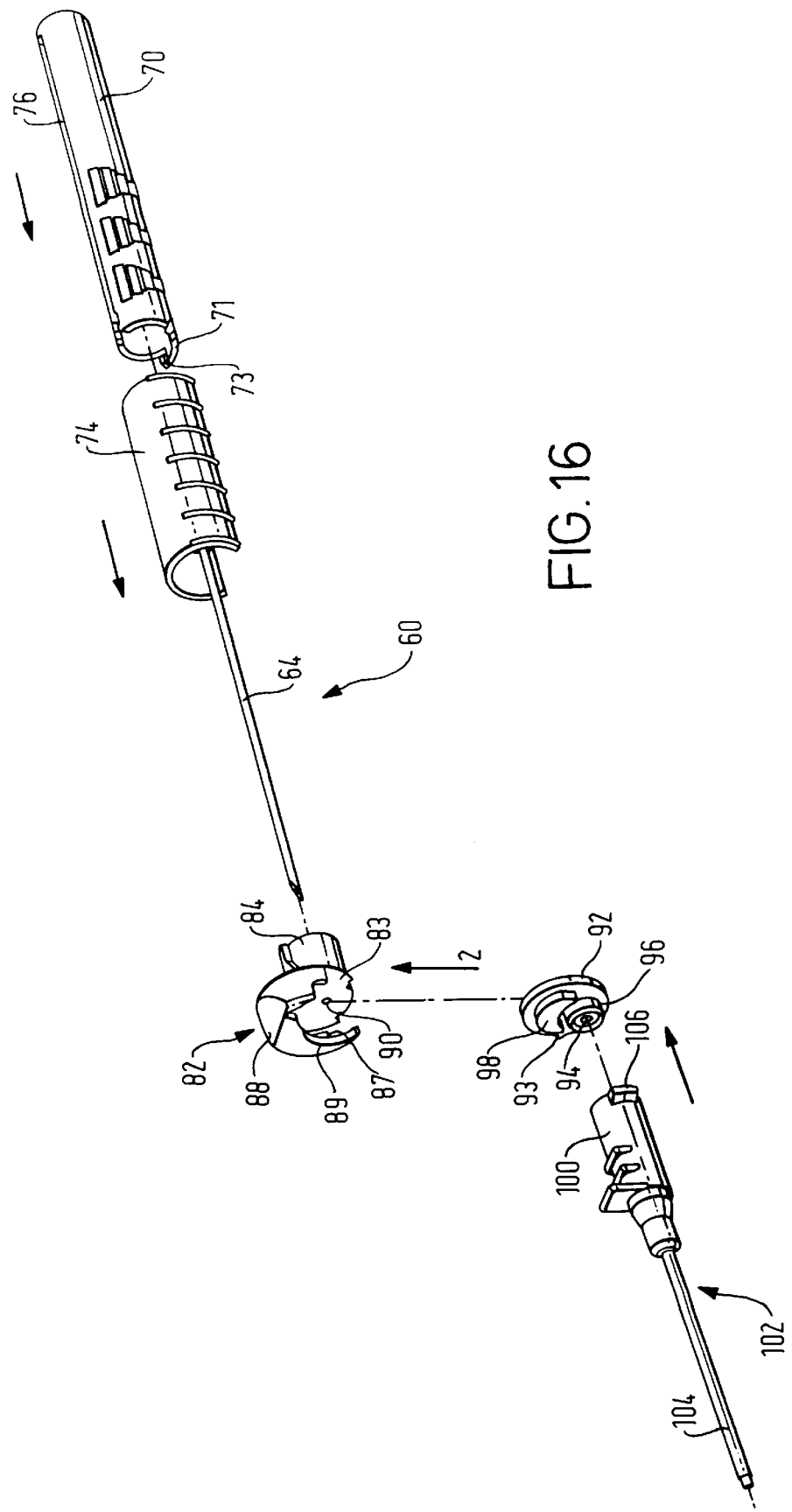
FIG. 16 is an exploded perspective view of the catheter assembly of FIG. 13.

Extending forwardly from the distal end of the housing 70 is a tongue 71 in which is formed a groove 73 (see FIGS. 13 and 16).

Fixedly mounted on the distal end of the housing 70 is a member 82 which comprises a plate 83 extending rearwardly from which is a tubular portion 84. As shown, the tubular portion 84 is fixed within the distal end of the housing 70 and includes a rearwardly extending boss 86. Extending forwardly from the plate 83 is a shroud portion 88 which includes a flange 89 depending from a forward face of the shroud portion 88, said flange 89 being spaced from the forward face of the plate 83. The flange 89 defines an abutment 87. A through hole 90 extends through the boss 86 and the plate 83 to communicate within the interior of the shroud portion 88.

A hub support member 92 is located within the shroud portion 88 such that it can rotate relative to the member 82 between a first position in which a hole 94 in the hub support member is aligned with the through hole 90 and a second position in which the holes 90, 94 are misaligned. The hub support member 92 includes on its forward facing surface a boss 96 for supporting a cannula hub 100 and spaced therefrom a latching protuberance 98 for preventing rotational movement of the cannula hub 100 relative to the hub support member 92. It will be apparent from FIG. 16 that the hole 90 and the boss 96 are offset from the centre of the hub support member 92.

Also formed on the hub support member 92 is a lug 93 which in a ready-for-use position engages the abutment 87.

The cannula hub 100 forms part of a cannula assembly 102 which also includes a hollow cannula 104 attached to the hub 100. Formed on the hub 100 at its proximal end are latching ears 106 which engage the latching protuberance 98.

Figure 14:
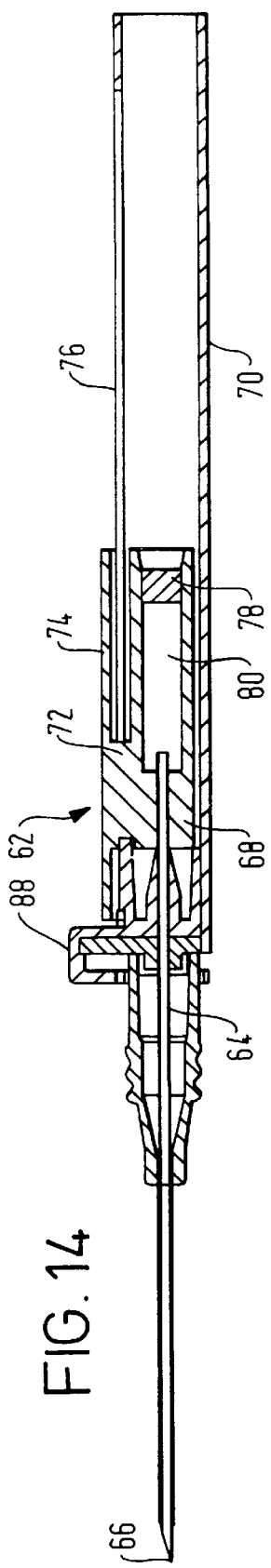
FIG. 14 is a longitudinal cross-section through the catheter assembly of FIG. 13.
Figure 19:
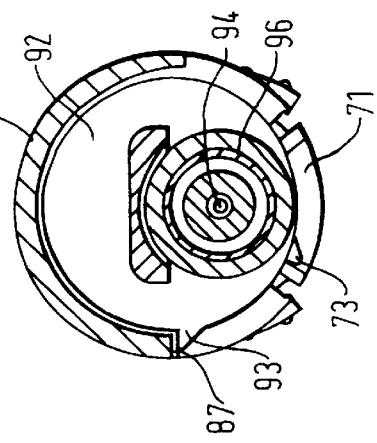
Figure 15:
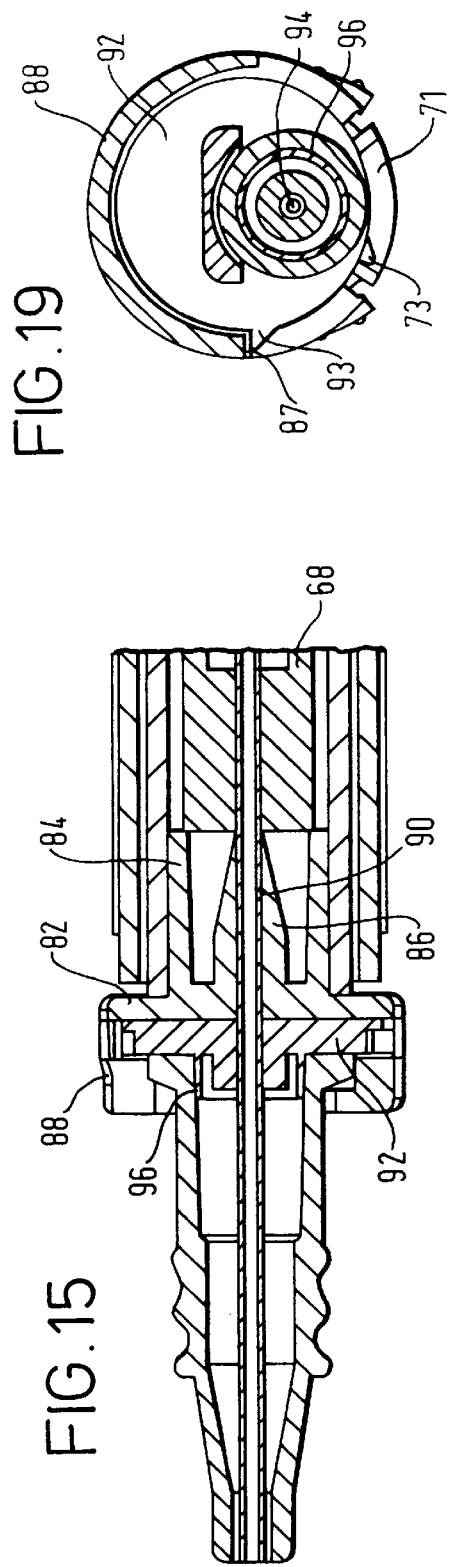
FIG. 15 is an enlarged cross-sectional detail of the catheter assembly of FIGS. 12 and 13.

In the ready-for-use position illustrated in FIGS. 13 to 15, the needle hub 68 is located at the forward end of the housing 70 such that the needle 64 extends through the holes 90, 94 and through the cannula assembly 102 with its sharp distal tip 66 extending outwardly from the free end of the hollow cannula 104. In this position, the cannula assembly 102 at its proximal end is supported by the boss 96 on the hub support member 92 and is locked in position by the flange 89 extending from the forward face of the shroud portion 88. In this position the hub support member 92 and the member 82 are prevented from relative rotational movement by the needle 64 and the lug 93 engages the abutment 87 (see FIG. 16).

Once penetration of the patient's skin has been effected, the gripper 74 is engaged to move the needle hub 68 along and towards the proximal end of the housing 70, that is, towards the position illustrated in FIG. 14. This movement of the needle hub 68 will cause the needle 64 to be withdrawn through the hollow cannula 104, the cannula hub 100 and back through the hole 94 until the needle tip 66 rests in the hole 90 in the member 82. When the needle tip 66 is clear of the hole 94, the housing 70 together with the member 82 is turned approximately 60 degrees relative to the hub support member 92 and the cannula assembly 102 (See FIG. 15). This has the effect of unlocking the cannula assembly 102 from the remainder of the catheter assembly 60. Further, the lug 93 in the hub support member 92 will latch into the groove 73 in the tongue 71 at the front of the housing 70 to prevent relative rotational movement of the hub support member 92 back towards its first relative position. In said second relative position it is clear that due to the miss-alignment of the holes 90, 94, the needle is prevented from longitudinal forward movement out from the housing 70.

As with the first embodiment, it follows that the cannula assembly 102 can only be detached from the remainder of the catheter assembly 60 after the needle tip 66 is completely contained within the housing 70.

I claim:

1. A medical device, comprising:

a needle having a proximal end and a sharp distal tip;

a needle hub connected to the proximal end of the needle;

a housing having a proximal portion, a distal portion, a longitudinal axis and a hole adjacent to the distal portion, the needle and needle hub being movably disposed in the housing between a retracted position and an extended position;

a latch having an opening for passage of the needle, the latch slidably mounted to the housing through the hole of the housing and movable laterally with respect to the housing between a first position and a second position, wherein the needle engages the latch in the retracted position and the extended position and when the needle and the needle hub are moved to the retracted position, the latch is slidable to move a distal portion of the needle so it is laterally offset from the longitudinal axis of the housing.

2. The medical device of claim 1 further comprising a spring dispose within the latch to bias the latch to the second position.

3. The medical device of claim 1 further comprising a catheter and a catheter hub affixed to the catheter wherein the needle extends through the catheter hub and catheter when the needle is in the extended position wherein the latch engages the catheter hub in the first position.

4. The medical device of claim 1 wherein the latch includes a latching member and the housing includes a protuberance that engages the latching member to lock the latch in the second position.

* * * * *